(12) United States Patent
Shimazu

(10) Patent No.: US 10,568,590 B2
(45) Date of Patent: Feb. 25, 2020

(54) RADIATION IMAGING APPARATUS

(71) Applicant: SHIMADZU CORPORATION, Nakagyo-Ku, Kyoto-Shi, Kyoto (JP)

(72) Inventor: Keisuke Shimazu, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 163 days.

(21) Appl. No.: 15/889,927

(22) Filed: Feb. 6, 2018

(65) Prior Publication Data

US 2018/0368787 A1 Dec. 27, 2018

(30) Foreign Application Priority Data

Jun. 23, 2017 (JP) ................................. 2017-122941

(51) Int. Cl.
| *A61B 6/04* | (2006.01) |
| *A61B 6/00* | (2006.01) |
| *A61B 6/06* | (2006.01) |

(52) U.S. Cl.
CPC .......... *A61B 6/0414* (2013.01); *A61B 6/0421* (2013.01); *A61B 6/06* (2013.01); *A61B 6/44* (2013.01); *A61B 6/4452* (2013.01); *A61B 6/487* (2013.01)

(58) Field of Classification Search
CPC ....... A61B 6/0414; A61B 6/0421; A61B 6/06; A61B 6/44; A61B 6/4452; A61B 6/487
See application file for complete search history.

(56) References Cited

U.S. PATENT DOCUMENTS

2010/0329414 A1* 12/2010 Zhu .......................... A61N 5/10
378/4
2011/0277236 A1* 11/2011 Moriarity ............... A61G 7/001
5/87.1

FOREIGN PATENT DOCUMENTS

JP 5218677 4/2013

* cited by examiner

*Primary Examiner* — Mark R Gaworecki
(74) *Attorney, Agent, or Firm* — Andrew F. Young, Esq.; Lackenbach Siegel, LLP

(57) ABSTRACT

A radiation imaging apparatus adds a compression force to the subject and a belt 31 separated from the surface of a table 13 moves to a lifting position by providing the belt 31 with tension and rotation of a wind-up roller 34 wherein in use belt 31 lifts from the surface of the table 13 and compresses the abdomen of the subject M and, after rotation of the wind-up roller 34 ends X-ray imaging occurs.

5 Claims, 10 Drawing Sheets

RADIATION IMAGING APPARATUS

CROSS REFERENCE TO RELATED APPLICATIONS

This application relates to, and claims priority from JP 2017-122941 filed Jun. 23, 2017, the entire contents of which are incorporated herein by reference.

FIGURE SELECTED FOR PUBLICATION

FIG. 4

BACKGROUND OF THE INVENTION

Field of the Invention

The present invention relates to a radiation imaging apparatus that performs a radiation imaging such as an X-ray imaging relative to a subject on a table.

Description of the Related Art

Such radiation imaging apparatus may include, for example, such as the X-ray imaging apparatus called a fluoroscopic imaging platform. Such X-ray imaging apparatus comprises a table that tilts while the subject is being loaded, an X-ray irradiation element that irradiates an X-ray to the subject, an X-ray detector that detects the X-ray, which is irradiated from the X-ray irradiation element irradiates, that transmits the subject; and performs the X-ray imaging or the X-ray fluoroscopy relative to the subject.

Relative to such X-ray imaging apparatus, for example, when an upper digestive tract including stomach and so forth is subjected to the X-ray imaging or the X-ray fluoroscopy, the X-ray imaging or the X-ray fluoroscopy may be performed while the upper digestive tract is deformed by compressing. In such case, when the X-ray imaging or the X-ray fluoroscopy is performed while the subject is in the supine posture (position), the upper digestive tract (gastrointestinal tract) is compressed with a compression tube (refer to the Patent Document 1).

On the other hand, when the X-ray imaging or the X-ray fluoroscopy is performed while the subject is in the prone (lying face-down) posture (position), the X-ray imaging or the X-ray fluoroscopy is performed by inserting a prone subject compression paddle (futon), which is made of e.g., the rounded towel and so forth between the abdomen of the subject and the table.

RELATED PRIOR ART DOCUMENTS

Patent Document

Patent Document 1: JP Patent 5218677 B1

ASPECTS AND SUMMARY OF THE INVENTION

Objects to be Solved

When the X-ray imaging or the X-ray fluoroscopy is performed using the prone subject compress paddle, the size of the prone subject compression paddle must be changed depending on the constitution of subject and the shape of the upper digestive tract thereof. In such case, an operator has to move from the operation room to the examination room and change the size of the prone subject compression paddle, and such work must be repeatedly carried out, so that the labor and the time for such preparation is inevitable. In addition, relative to the prone position double contrast imaging, when such imaging may be required while lowering head up to 45 degrees, and the preparation work for such imaging takes a longer time, the burden for the subject can be high.

The purpose of the present invention is to solve the above objects and to provide an X-ray imaging apparatus that facilitates to add a compression force to the subject.

Means for Solving the Problem

According to on adaptive aspect of the present invention, there is provided a radiation imaging apparatus comprising a table that tilts and moves while a subject is loaded, a radiation irradiation element that irradiates a radiation to the subject who is loaded on the table, a radiation detector that detects a radiation that is irradiated from the radiation irradiation element and transmits through the subject, a belt member that is crossing to a body-axis of the subject who is loaded on the table, and a belt lifting-and-lowering mechanism that allows at least a part of the subject, which is loaded on the table, to separate from the table surface by changing a distance between the belt and the table surface.

According to the another adaptive and alternative aspect of the present invention, there is provided a radiation imaging apparatus, wherein the belt lifting-and-lowering mechanism comprises a pair of guide members at both ends of the table in the direction crossing to the body axis direction of the subject that guides the belt to the position separate from the table surface, and a tension adjustment mechanism that changes the distance between the belt and the table surface by changing the tension provided to the belt.

According to the another adaptive and alternative aspect of the present invention, there is provided a radiation imaging apparatus, wherein one end of the belt is connected to the upper portion of one of the pair of the guide members, and the other end of the belt bridges over the surface of the upper portion of the other one of the pair of the guide members followed by winded up by the wind-up mechanism.

According to the another adaptive and alternative aspect of the present invention, there is provided a radiation imaging apparatus, wherein a belt lifting-and-lowering mechanism changes the distance between the belt and the table surface by lifting the support position of the belt.

According to the another adaptive and alternative aspect of the present invention, there is provided a radiation imaging apparatus, wherein a belt lifting mechanism further comprises a wind-up member having an elliptical-shape or oblong-shape cross section capable of winding up the belt onto the circumference portion thereof, wherein the wind-up member changes the rotation angle position thereof, so that the support position of the belt lifts, and as results, the distance between the belt and the table surface changes thereby.

Effect of the Invention

According to one alternative aspect of the invention, the belt lifting-and-lowering mechanism acts to lift-and-lower the belt, so that such mechanism can facilitate to provide the subject with a compression force. Therefore, the operator no longer repeatedly needs to change the size of the prone subject compression paddle, and in addition, the burden on the subject can be alleviated.

According to one alternative aspect of the invention the operator can easily adjust the compression force against the subject by changing the tension added to the belt.

According to one alternative aspect of the invention the operator can easily adjust the compression force against the subject by winding up the belt to change the tension added to the belt.

According to one alternative aspect of the invention the operator can easily adjust the compression force against the subject by changing the supporting position of the belt.

According to one alternative aspect of the invention, the operator can easily adjust the compression force against the subject by changing the rotation angle position of the wind-up member having an elliptical-shape or oblong-shape cross section.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
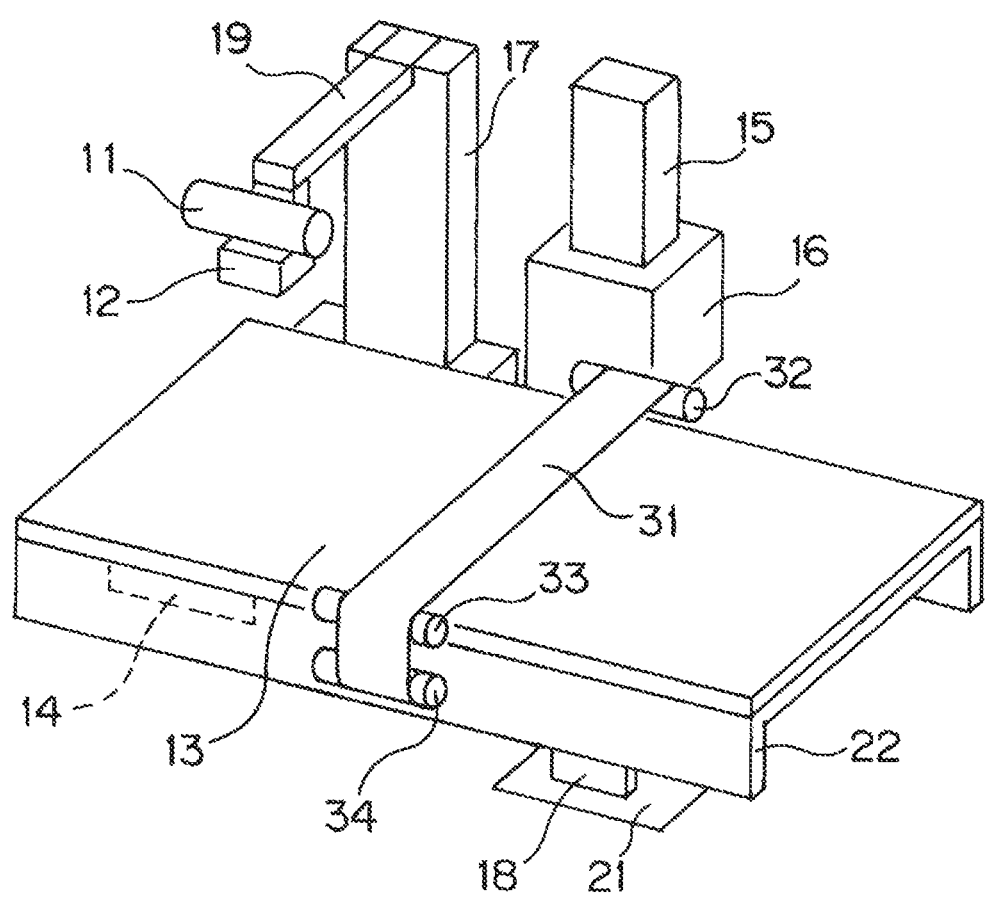
FIG. 1 is a perspective view illustrating an X-ray fluoroscopy imaging apparatus according to the aspect of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations nay be described as multiple discrete operations in turn, in a manner that may be helpful in understanding embodiments of the present invention; however, the order of description should not be construed to imply that these operations are order dependent.

Figure 2:
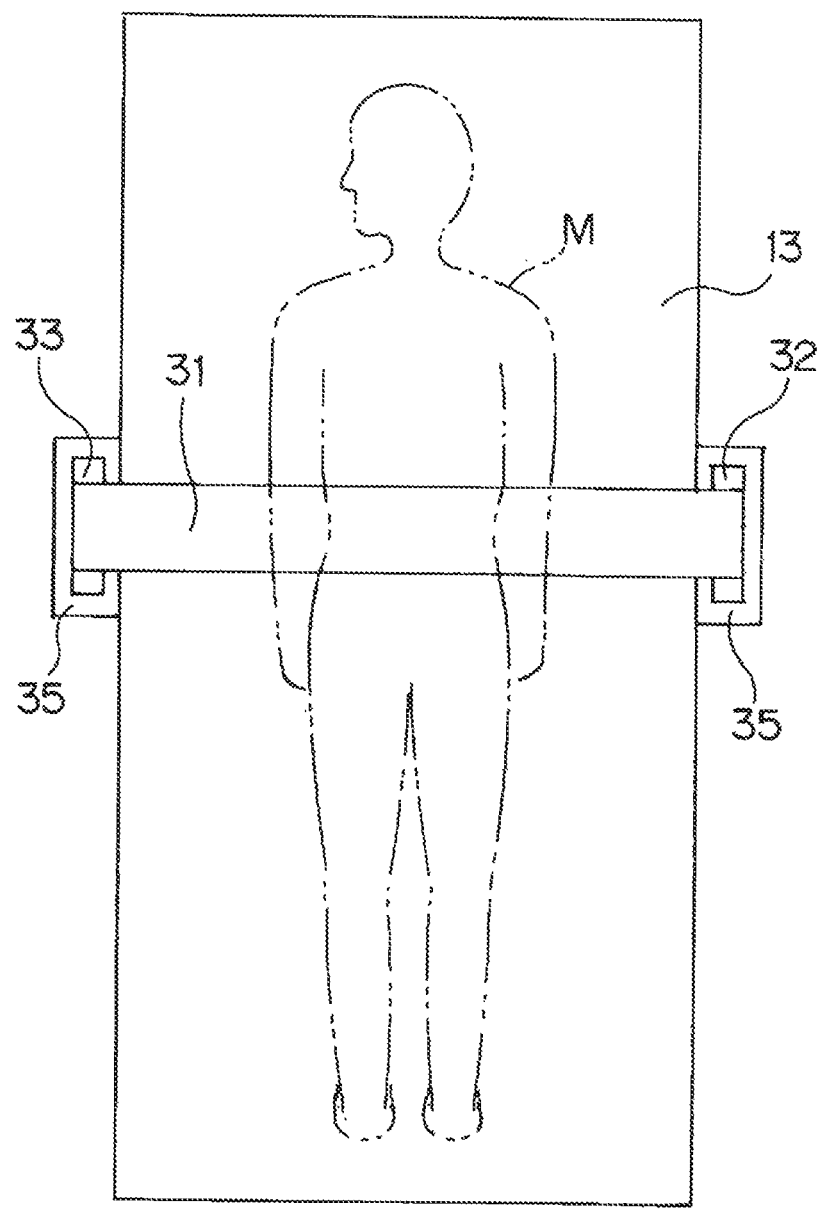
FIG. 2 is a schematic plan view illustrating the prone subject M on the table 13.

*The inventor sets forth Embodiments of the present invention based on the following FIGs. FIG. 1 is a perspective view illustrating an X-ray fluoroscopy imaging apparatus as the X-ray imaging apparatus according to the aspect of the present invention. FIG. 2 is a schematic plan view illustrating that the prone subject M is loaded on the table 13. In addition, the housing 35 is not shown in FIG. 1.

Such X-ray fluoroscopy imaging apparatus, called the fluoroscopy imaging platform comprises; a main support column 15 that is connected to the support leg 18 that is installed on the pedestal 21; a holding element 16 that is liftable-and-lowerable relative to the main support column 15; a support frame 22 that is connected rotatably to the holding element 16; a table 13 that is installed on the support frame 22; a support column 17 having an arm 19 that supports an X-ray tube 11 and a collimator 12; and an X-ray detector 14, such as the flat panel detector and so forth, that is installed at the location under the surface of the table 13 to face the X-ray tube 11.

The holding element 16 is shiftable-and-lowerable along with the main support column 15. In addition, the table 13 and the support frame 22 rotate around the axis, which is orthogonal to the longitudinal direction of the table 13 and facing the horizontal direction, as the center thereof. In such way, the table 13 tilts and moves. In addition, the support column 17 and the X-ray detector 14 shifts back-and-forth in synchronism with each other in the longitudinal direction of the table 13. Further, the X-ray tube 11 and the collimator 12 lift-and-lower along the support column 17 together with the arm 19. And the support column 17 rotates around the axis, which is orthogonal to the longitudinal direction of the table 13 and facing the horizontal direction, as the center thereof in synchronism with the table 13 and the support frame 22. The imaging system having the X-ray tube 11, the collimator 12 and the X-ray detector 14 rotates as well in accordance with rotation of the support column 17.

When the X-ray fluoroscopy or the X-ray imaging for the subject M is performed, the subject M is loaded on the table 13 following arranging the table 13 to the location at which the surface thereof faces approximately the vertical direction. The table 13 can tilt until the required angle for the X-ray fluoroscopy or the X-ray imaging according to necessity. For example, when performing the lower-head prone position double contrast imaging, the table 13 is tilted up to 45 degrees to perform the X-ray fluoroscopy.

The belt 31, made of a cloth, extending in the crossing direction to the body-axis direction of the subject M loaded on the table 13 is installed on the table 13. Such belt 31 lift-and-lowers between the waiting position at which loaded on the table 13 and the lifting position at which separated from the table 13 to separate the abdomen of the subject M from the table 13 by the belt lifting-and-lowering mechanism.

Figure 3:
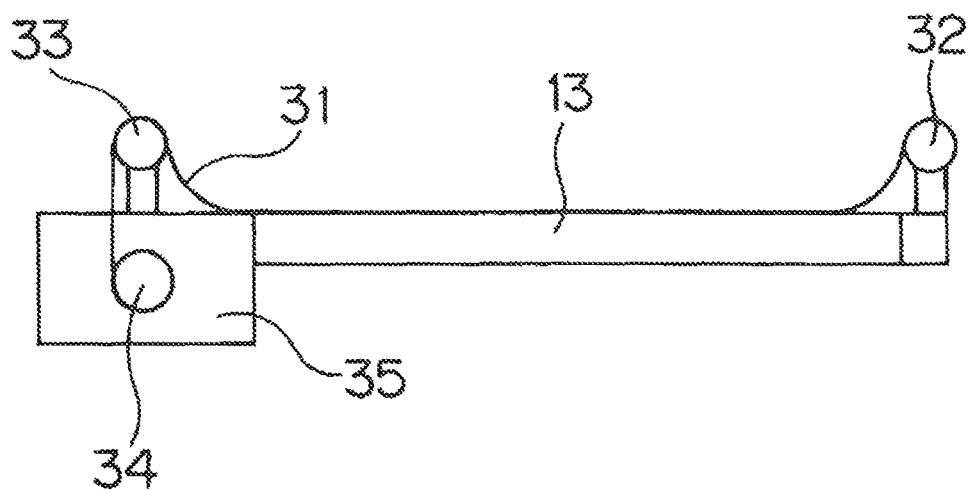
FIG. 3 is a schematic diagram illustrating a belt lifting-and-lowering mechanism according to the aspect of the Embodiment 1 of the present invention.
Figure 4:
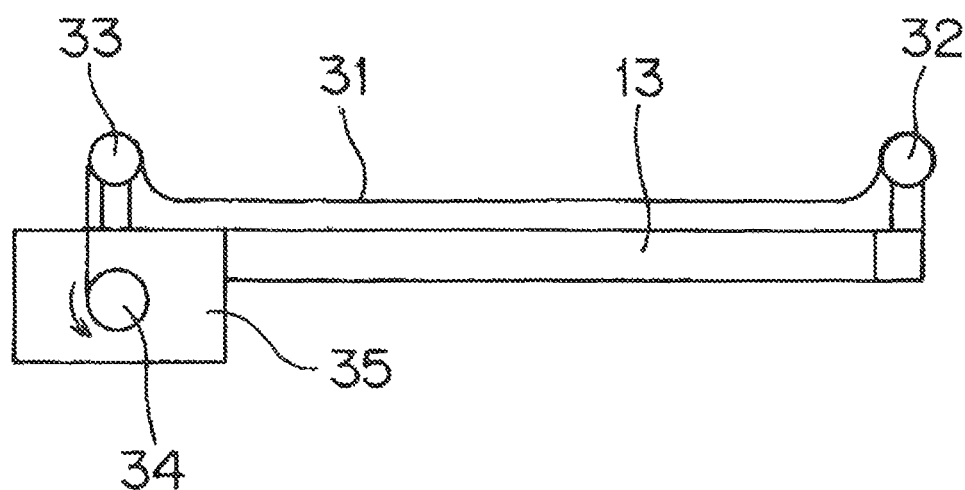
FIG. 4 is a schematic diagram illustrating a belt lifting-and-lowering mechanism according to the aspect of the Embodiment 1 of the present invention.

FIG. 3, FIG. 4 are schematic diagrams illustrating a belt lifting-and-lowering mechanism according to the aspect of the Embodiment 1 of the present invention. In addition, FIG. 3 is illustrating the state in which the belt 31 is in-place in the waiting position, and FIG. 4 is illustrating the state in which the belt 31 is in-place in the lifting position.

According to the aspect of the Embodiment 1, the belt lifting-and-lowering mechanism comprises a pair of guide members 32, 33 that guide the belt 31 to the location separated from the surface of the table 13 (table 13 surface) at the both ends of the direction (right to left direction referring to FIG. 2-FIG. 4) crossing to the body-axis direction of the subject M, and the wind-up roller 34 is installed in the housing 35 and rotates when the motor, not shown in FIG. is driven. Such belt lifting-and-lowering mechanism rotates the wind-up roller 34, and winds up the one end of the belt 31 by the wind-up roller 34 to change the tension to be provided to the belt 31, so that the distance between the belt 31 and the surface of the table 13 can be changed.

Referring to FIG. 3, when the X-ray fluoroscopy imaging apparatus having the belt lifting-and-lowering mechanism according to the aspect of the Embodiment 1 performs the X-ray fluoroscopy or the X-ray imaging, the belt 31 is in-place in the waiting position. And the prone subject M is loaded on the belt 31 and the table 13. Then after, referring to FIG. 4, the belt 31 that is separated from the surface of the table 13 moves to the lifting position by providing the belt 31 with a tension along with the rotation of the wind-up roller 34.

Accordingly, the belt 31 that lifts from the surface of the table 13 compresses the abdomen of the subject M. Once the belt 31 is winded up by the wind-up roller 34 along with the rotation of the wind-up roller 34 until reaching the appropriate state in which the abdomen of the subject M to be compressed separated from the surface of the table 13, and after the rotation of the wind-up roller 34 suspends, and the x-ray fluoroscopy or the X-ray imaging is performed. In addition, after the height of the belt 31 is adjusted to the appropriate position for the X-ray fluoroscopy or the X-ray imaging by changing the tension against the belt 31 while performing the X-ray fluoroscopy and checking the X-ray fluoroscopic image, the X-ray fluoroscopy or the X-ray imaging may be started.

In such way, when the belt lifting-and-lowering mechanism according to the aspect of the Embodiment 1 is used, the belt 31 lifts by winding the belt 31 with the wind-up roller 34, so that such belt 31 can compress the abdomen of the subject M. And the belt 31 lifts and lowers, so that the compression force against the subject M can be easily changed. Therefore, the operator no longer repeatedly needs to change the size of the prone subject compression paddle, and in addition, the burden on the subject M can be alleviated.

Figure 5:
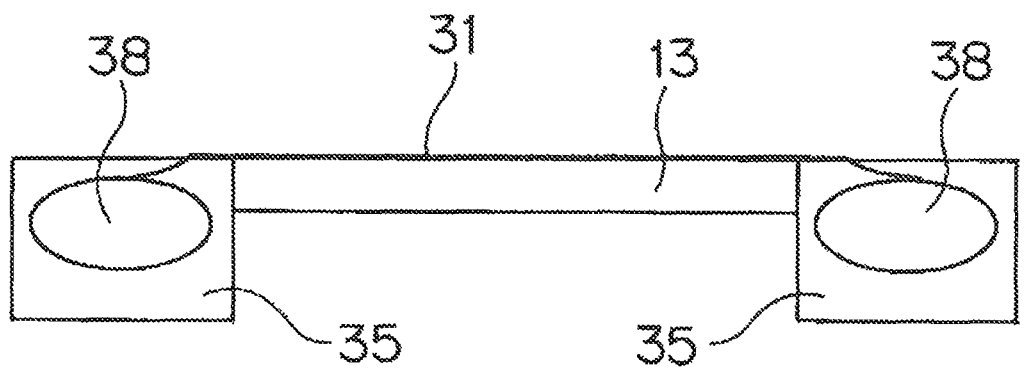
FIG. 5 is a schematic diagram illustrating a belt lifting-and-lowering mechanism according to the aspect of the Embodiment 2 of the present invention.
Figure 6:
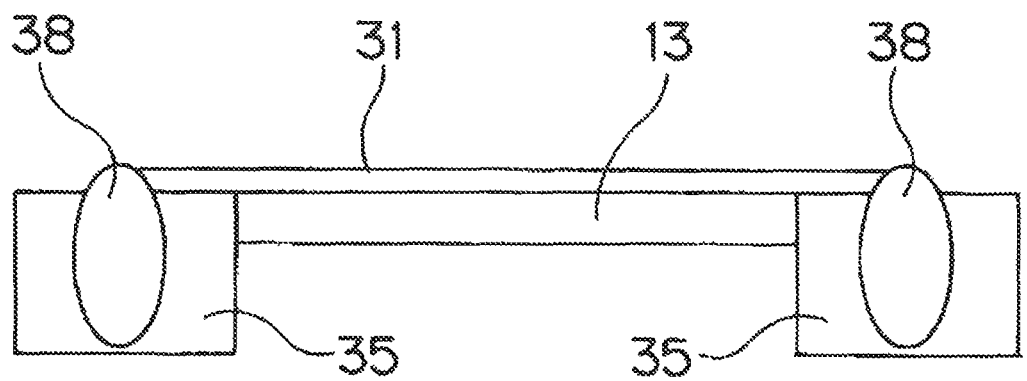
FIG. 6 is a schematic diagram illustrating a belt lifting-and-lowering mechanism according to the aspect of the Embodiment 2 of the present invention.

Next, the inventor sets forth the other Embodiment of the present invention. FIG. 5, FIG. 6 are schematic diagrams illustrating a belt lifting-and-lowering mechanism according to the aspect of the Embodiment 2 of the present invention. In addition, FIG. 5 is illustrating the state in which the belt 31 is in-place in the waiting position, and FIG. 6 is illustrating the state in which the belt 31 is in-place in the lifting position.

According to the aspect of the Embodiment 2, the belt lifting-and-lowering mechanism comprises a pair of wind-up members 38 connected to both ends of the belt 31 at the end portion in the crossing direction to the body-axis direction of the subject M relative to the table 13 (right-and-left direction in FIG. 2-FIG. 4). Such wind-up members 38 have an elliptical-shape cross-section, of which the circumference portion can wind up the belt 31. In addition, the elliptical shape can be replaced with an oblong shape. Such wind-up members 38 rotates due to driving of the motor, not shown in FIG., installed in the housing 35. Such belt lifting-and-lowering mechanism rotates the wind-up member 38 and winds up the belt 31 by the wind-up member 38, and also changes the height of the position of the belt 31 and the tension provided to the belt 31, so that the distance between the belt 31 and the surface of the table 13 can be changed.

Referring to FIG. 5, when the X-ray fluoroscopy imaging apparatus having the belt lifting-and-lowering mechanism according to the aspect of the Embodiment 2 performs the X-ray fluoroscopy or the X-ray imaging, the pair of the wind-up members 38 take a posture so that the long-axis of the cross-section of the elliptical shape faces the horizontal direction, so that the belt 31 can be in-place in the waiting position. And the prone subject M is loaded on the belt 31 and the table 13. Then after, the supporting position of the belt 31 lifts by rotating the wind-up members 38, so that a tension is provided to the belt 31, and consequently, the belt 31 moves to the lifting position that is separated from the surface of the table 13.

Accordingly, the belt 31 that lifts from the surface of the table 13 compresses the abdomen of the subject M, which separates from the surface of the table 13 thereby. Referring to FIG. 6, the pair of the wind-up members 38 takes a position at which the long-axis of the cross-section of the elliptical shape faces the vertical direction, so that the abdomen of the subject M can be compressed until attaining the appropriate state for the imaging.

Figure 7:
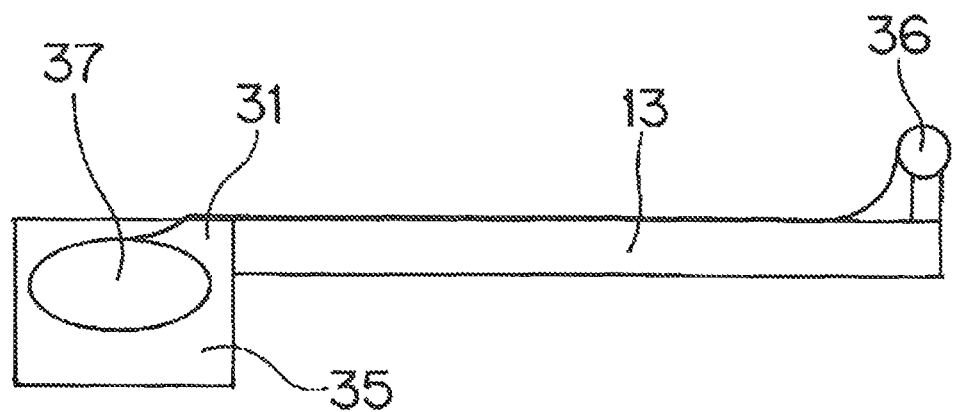
FIG. 7 is a schematic diagram illustrating a belt lifting-and-lowering mechanism according to the aspect of the Embodiment 3 of the present invention.
Figure 8:
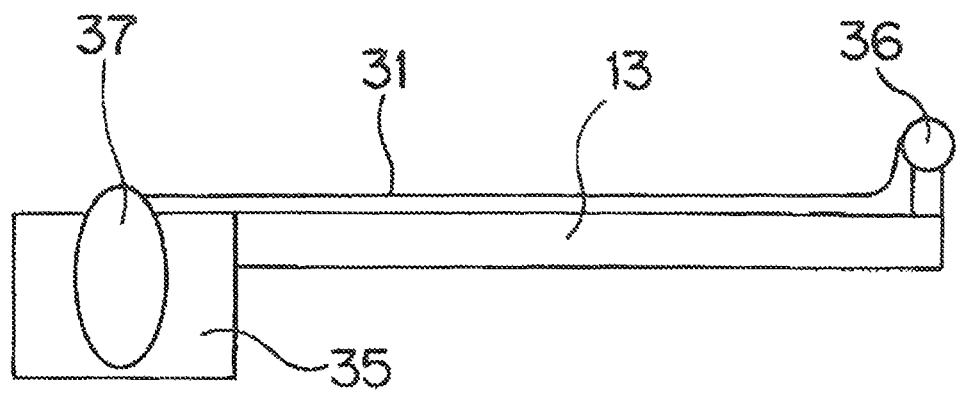
FIG. 8 is a schematic diagram illustrating a belt lifting-and-lowering mechanism according to the aspect of the Embodiment 3 of the present invention.

Next, the inventor further sets forth the other Embodiment of the present invention. FIG. 7, FIG. 8 are schematic diagrams illustrating a belt lifting-and-lowering mechanism according to the aspect of the Embodiment 3 of the present invention. In addition, FIG. 7 is illustrating the state in which the belt 31 is in-place in the waiting position, and FIG. 8 is illustrating the state in which the belt 31 is in-place in the lifting position.

The belt lifting-and-lowering mechanism according to the aspect of the Embodiment 3, comprises the support member 36, which is the same as the guide member 32, referring to FIG. 3, FIG. 4, at the one end of the crossing direction (right-to-left direction in FIG. 2-FIG. 4) of the body-axis of the subject M relative to the table 13, and the other end of the belt 31 is fixed to the support member 36. In addition, referring to FIG. 5, FIG. 6, the wind-up member 37 having the elliptical-shape cross-section, of which the circumference portion can wind up the belt 31, is installed to the opposite side of the support member 36, and one end of the belt 31 is fixed to the wind-up member 37.

Referring to FIG. 7, when the X-ray fluoroscopy imaging apparatus having the belt lifting-and-lowering mechanism according to the aspect of the Embodiment 3 performs the X-ray fluoroscopy or the X-ray imaging, the wind-up members 37 take a posture so that the long-axis of the cross-section of the elliptical shape faces the horizontal direction, so that the belt 31 can be in-place in the waiting position. And the prone subject M is loaded on the belt 31 and the table 13. Then after, the belt 31 that is separated from the surface of the table 13 moves to the lifting position by providing the belt 3 with a tension along with the rotation of the wind-up member 37.

Accordingly, the belt 31 that lifts from the surface of the table 13 compresses the abdomen of the subject M, which separates from the surface of the table 13 thereby. Referring to FIG. 8, the pair of the wind-up members 37 takes, a position at which the long-axis of the cross-section of the elliptical shape faces the vertical direction, so that the abdomen of the subject M can be compressed until attaining the appropriate state for the imaging.

Figure 9:
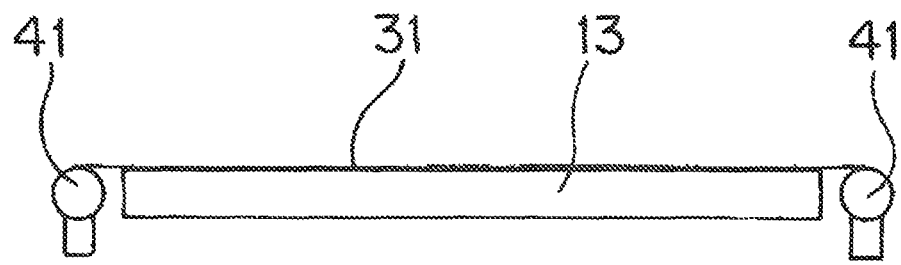
FIG. 9 is a schematic diagram illustrating a belt lifting-and-lowering mechanism according to the aspect of the Embodiment 4 of the present invention.
Figure 10:
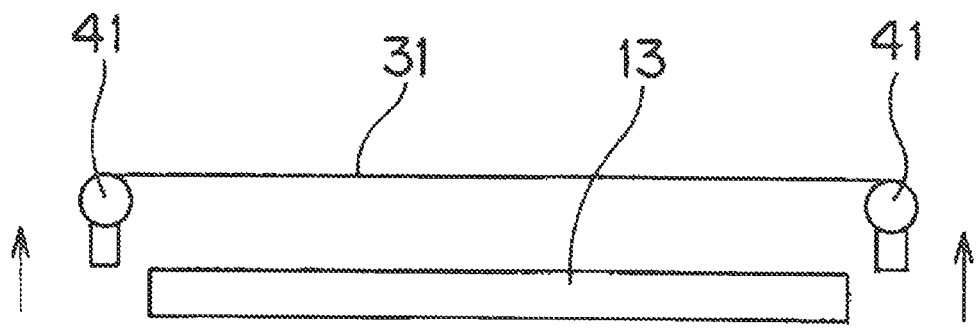
FIG. 10 is a schematic diagram illustrating a belt lifting-and-lowering mechanism according to the aspect of the Embodiment 4 of the present invention.

Next, the inventor further sets forth the other Embodiment of the present invention, FIG. 9. FIG. 10 are schematic diagrams illustrating a belt lifting-and-lowering mechanism according to the aspect of the Embodiment 4 of the present invention. In addition, FIG. 9 is illustrating the state in which the belt 31 is in-place in the waiting position, and FIG. 10 is illustrating the state in which the belt 31 is in-place in the lifting position.

According to the aspect of the Embodiment 4, the belt lifting-and-lowering mechanism comprises a pair of lifting-and-lowering members 41 connected to both ends of the belt 31 at the end portion in the crossing direction to the body axis direction of the subject M relative to the table 13 (right-and-left direction in FIG. 2-FIG. 4). Such lifting-and-lowering members 41 lifts and lowers in synchronism with each other by the lifting-and-lowering mechanism, not shown in FIG.

Referring to FIG. 9, when the X-ray fluoroscopy imaging apparatus having the belt lifting-and-lowering mechanism according to the aspect of the Embodiment 4 performs the X-ray fluoroscopy or the X-ray imaging, the pair of the lifting-and-lowering members 41 lowers, so that the belt 31 can be in-place in the waiting position. And the prone subject M is loaded on the belt 31 and the table 13. Then after the belt 31 that is separated from the surface of the table 13 moves to the lifting position by lifting the pair of the lifting-and-lowering member 41. Accordingly, the belt 31 that lifts from the surface of the table 13 compresses the abdomen of the subject M, which separates from the surface of the table 13 thereby. Referring to FIG. 10, the pair of the lifting-and-lowering members 41 lifts to the appropriate height, so that the abdomen of the subject M can be compressed until attaining the appropriate state for the imaging.

As used herein, an electronic or computer-type system may include but are not limited to, and without limitation, an input device for receiving data in a tangible form (e.g., data feed, data signals, etc.), an output device for outputting data in tangible form (e.g. data feed, data signals, printing or displaying data on a computer screen), a memory for storing data as well as computer code, and a processor (micro or otherwise) for executing computer code wherein said computer code resident in said permanent memory will physically cause said microprocessor to read-in data via said input device, process said data within said microprocessor and output said processed data via said output device.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

REFERENCE OF SIGNS

11 X-ray tube
12 Collimator
13 Table
14 X-ray detector
15 Main support column
16 Holding element
17 Support column
18 Support leg
19 Arm
31 Belt
32 Guide member
33 Guide member
34 Wind-up roller
36 Support member
37 Wind-up member
38 Wind-up member
41 Lifting mechanism
M Subject

What is claimed is:

1. A radiation imaging apparatus, comprising:
a table that tilts and moves while a subject is loaded on a support surface;
a radiation irradiation element that irradiates a radiation to said subject that is loaded on said table;
a radiation detector that detects the radiation that is irradiated from said radiation irradiation element and transmits through said subject during a use;
a belt having extending in a crossing direction to a body-axis of said subject that is loaded on said table; and
a belt lifting-and-lowering mechanism that allows at least a part of said subject which is loaded on said table, to separate from said table surface of said table by changing a distance between said belt and said table surface, the belt lifting-and-lowering mechanism comprising:
a pair of guide members that guides said belt to a position separate from said table surface, at both end of said table in the crossing direction to said body-axis direction of said subject; and
a tension adjustment mechanism that changes said distance between said belt and said table surface by changing a tension provided to said belt.

2. The radiation imaging apparatus, according to claim 1, wherein:
one end of said belt is connected to an upper portion of one of said pair of guide members, and another end of said belt that bridges over a surface of the upper portion of the other one of said pair of the guide members is wound up by a wind-up mechanism.

3. The radiation imaging apparatus, according to claim 1, wherein:
said belt lifting-and-lowering mechanism changes said distance between said belt and said table surface by lifting a support position of said belt.

4. The radiation imaging apparatus, according to claim 3, wherein:
said belt lifting mechanism further comprises:
a wind-up member;
said wind-up member having at least one cross-section of an elliptical-shape and an oblong-shape, that winds up said belt onto a circumference portion thereof, wherein said wind-up member changes a rotation angle position thereof, so that a support position of said belt lift-and-lowers to change said distance between said belt and said table surface.

5. A radiation imaging apparatus, comprising:
a table that tilts and moves while a subject is loaded on a support surface;
a radiation irradiation element that irradiates a radiation to said subject that is loaded on said table;
a radiation detector that detects the radiation that is irradiated from said radiation irradiation element and transmits through said subject during a use;
a belt having extending in a crossing direction to a body-axis of said subject that is loaded on said table; and
a lifting-and-lowering mechanism that allows at least a part of said subject which is loaded on said table, to separate from said table surface of said table by changing a distance between said belt and said table surface, said belt lifting-and-lowering mechanism changes said distance between said belt and said table surface by lifting a support position of said belt, said belt lifting mechanism comprising:
a wind-up member;
said wind-up member having at least one cross-section of an elliptical-shape and an oblong-shape, that winds up said belt onto a circumference portion thereof, wherein said wind-up member changes a rotation angle position thereof, so that a support position of said belt lift-and-lowers to change said distance between said belt and said table surface.

* * * * *